United States Patent [19]

Monchalin et al.

[11] Patent Number: 5,608,166
[45] Date of Patent: Mar. 4, 1997

[54] GENERATION AND DETECTION OF ULTRASOUND WITH LONG PULSE LASERS

[75] Inventors: Jean-Pierre Monchalin; Alain Blouin, both of Montréal, Canada

[73] Assignee: National Research Council of Canada, Ottawa, Canada

[21] Appl. No.: 542,337

[22] Filed: Oct. 12, 1995

[51] Int. Cl.$^6$ .................................................. G01N 29/00
[52] U.S. Cl. .................................................. 73/657; 73/655
[58] Field of Search ............................. 73/601, 643, 655, 73/656, 657

[56] References Cited

U.S. PATENT DOCUMENTS

| | | | |
|---|---|---|---|
| 4,633,715 | 1/1987 | Monchalin | 73/657 |
| 4,659,224 | 4/1987 | Monchalin | 73/657 |
| 4,966,459 | 10/1990 | Monchalin et al. | 356/358 |
| 5,080,491 | 1/1992 | Monchalin | 73/657 |
| 5,131,748 | 7/1992 | Monchalin et al. | 356/349 |
| 5,137,361 | 8/1992 | Heon et al. | 356/352 |

OTHER PUBLICATIONS

Modulated Laser Array Sources for Generation of Narrowband and Directed Ultrasound. James W. Wagner; Andrew D. W. McKie; James B. Spicer; and John B. Deaton, Jr. Journal of Nondestructive Evaluation, vol. 9, No. 4, 1990 (no month).

Progress in Pulsed Laser Array Techniques for Generation of Acoustic Waves. Todd W. Murray; James W. Wagner. Review of Progress in Quantitative Nondesructive Evaluation vol. 13, pp. 532–539, 1994 (no month).

Temporal modulation of a laser source for the generation of ultrasounic waves. R. Pierce; C. Ume; and J. Jarzynski. Ultrasonics 1995 vol. 33. No.. 2. (no month) pp. 133–137.

New technique of photodisplacement imaging using one laser for both excitation and detection. Chen L.; Yang K. H.; Zhang S. Y. Applied Physics Letter vol. 50. No. 19. pp. 1349–1351, May 1987.

Holographic currents and the non–steady–state photoelectromotive force in cubic photorefractive crystals. L. A. Sokolov; S. I. Stepanov; and G. S. Trofimov. Optical Society of America vol. 9. No. 1/Jan. 1992, pp. 173–176.

Photodisplacement techniques for defect detection. Y. Martin Y; E. A. Ash. Philosophical Transactions of the Royal Society of London, vol. 320, No. 1554, pp. 257–269, 1986 (no month).

*Primary Examiner*—Christine K. Oda
*Attorney, Agent, or Firm*—Neil Teitelbaum & Associates

[57] ABSTRACT

A method and apparatus for generating and detecting ultrasound on a workpiece utilizing a long pulse laser. A modulated pulsed laser beam is directed at the workpiece. The pulse duration is defined to be the time of propagation of ultrasound from a generation location to a flaw or discontinuity to be detected within the workpiece and then to a detection location, or, the time of propagation of ultrasound directly from the generation location to the detection location. A second pulsed laser beam, having a pulse duration longer than the ultrasonic propagation time, is also directed at the workpiece. After receiving phase modulated light from second pulsed laser beam reflected or scattered by the workpiece, phase modulated light is demodulated to obtain a demodulation signal representative of the ultrasonic motion at the surface of the workpiece. The demodulation signal is then electronically processed.

23 Claims, 7 Drawing Sheets

PRIOR ART　　　FIG. 1

GENERATION AND DETECTION OF ULTRASOUND WITH LONG PULSE LASERS

FIELD OF THE INVENTION

This invention relates to a method and an apparatus for generating and detecting ultrasound at a distance with two long pulse lasers or a single long pulse laser.

BACKGROUND OF THE INVENTION

A long pulse laser is defined herein as a laser with a pulse duration that exceeds the ultrasonic propagation time between the generation and detection locations at the surface of the workpiece. In the instance where the technique is applied to the detection of a discontinuity or flaw within or at the surface of the workpiece and where the generation and detection locations are on the same side of the workpiece and eventually superimposed, this propagation time is the time for ultrasound to propagate from the generation location to the discontinuity or flaw and subsequently from the discontinuity or flaw to the detection location; or, stated differently, it can be said that the pulse duration of a long pulse laser is sufficient in length to allow the capture of several ultrasonic echoes from such a discontinuity or flaw.

Ultrasonics is very powerful technique for inspecting and characterizing materials or industrial products. It allows the measurement of the thickness of parts to be determined, knowing the propagation velocity in the material. It is also widely used for detecting flaws in material. One important application is the detection of delaminations in polymer-matrix composite materials used in advanced aeronautic and aerospace structures. By performing several measurements along appropriate directions, ultrasonics also allows the determination of the elastic constants of the material. Furthermore, ultrasonics could be used for the determination of anisotropy or preferred crystallographic orientation (texture). One example of application is the determination of the texture of steel sheets by the generation of surface or plate waves in various directions. Texture is important for the deep drawing of such steel sheets, a forming process used for making parts of a car body or beverage cans.

Ultrasonics is usually applied by using piezoelectric transducers for the generation and detection of ultrasound. Ultrasonic coupling requires the transducers to be either in contact with the workpiece or to operate in immersion (usually in water). Such approaches are obviously not applicable at high temperatures. Another practical requirement is the orientation of the transducer in a direction approximately normal to the surface of the workpiece, which makes the inspection of pieces with complex geometry difficult or impossible. These limitations are eliminated by using lasers for the generation and detection of ultrasound. In this technique, called laser-ultrasonics (see prior art FIG. 1), a short pulse laser 10 is used for the generation of ultrasound. Pulse duration determines the frequency range of ultrasound that is generated, typically in the MHz range, thus durations of about 100 ns or shorter have been required. A long pulse laser 12 or a continuous laser is used for detection. A pulsed detection laser is preferable to a continuous laser, since it provides higher output power, it provides greater detection sensitivity. The duration of the pulse of the detection laser should be sufficiently long to capture all the ultrasonic echoes, which means, for most industrial applications, a pulse duration of more than 10 µs is preferred. The requirement of generating frequencies in the MHz range apparently forbids the use of a long pulse laser (10 µs and higher) for generation, and, as a consequence, prevents the use of the same laser for generation and detection. However, using the same laser for generation and detection would be desirable, reducing the laser hardware and the relatively high cost associated with this technique. As described later, the applicants have found that generation and detection of ultrasound with two long pulse lasers or even a single one is indeed possible and have shown that systems using such lasers could be applied to many situations of practical interest.

As will be described below, this invention is first based on the intensity modulation of the generation laser beam. Although modulated laser beams have been previously reported for the generation of ultrasound (see for example "Modulated laser array sources for the generation of narrowband and directed ultrasound", by J. W. Wagner, A. D. W. McKie, J. B. Spicer and J. B. Deaton, published in Journal of Nondestructive Evaluation, vol. 9, no 4, 1990, pp.263–270 and "Progress in pulsed laser array techniques for generation of acoustic waves", by T. W. Murray and J. W. Wagner, published in Review of Quantitative Nondestructive Evaluation, vol. 13, 1994, pp. 533–539), the duration of laser excitation has been typically relatively short, which is affirmed by the fact that in all the reported works the various ultrasonic echoes are resolved. The approach used in these reported works consists more specifically of using multiple short laser pulses in sequence and is the optical counterpart of the tone burst approach used in conventional ultrasonics. The practical interest of this approach is the increase of sensitivity which occurs at the repetition pulse frequency. The invention described in the present application applies instead to much longer pulse durations, which make the ultrasonic echoes to get mixed or the received signal to last a long time, comparable to the duration of the detection laser pulse. As a result, this requires an innovative approach which is described hereafter. It is also noted also that the use of a modulated long laser pulse (of duration comparable to the one considered here) for generation of ultrasound has been reported by R. Pierce, C. Ume and J. Jarzynski in Ultrasonics, vol. 33, no 2, 1995, pp. 133–137 (Title: Temporal modulation of a laser source for the generation of ultrasonic waves). This reported work uses conventional piezoelectric detection and not optical detection and does not address the problem of overlapping echoes, since a particular detection configuration and a special test block was used.

Modulated laser beams have also been used for photodisplacement imaging and there have been reports of the use of a single laser for generation and detection (see "Photodisplacement techniques for defect detection" by Y. Martin and E. A. Ash published in Philosophical Transactions of the Royal Society of London A (Mathematical and Physical Sciences), vol. 320, 1986, pp. 257–269 and "New technique of photodisplacement imaging using one laser for both excitation and detection" by L. Chen, K. H. Yang and S. Y. Zhang published in Applied Physics Letters, vol. 50, 1987, pp. 1349–1351). It should first be noted that photodisplacement imaging is based on the detection of the initial surface deformation produced by laser absorption and not on the detection of ultrasound. This technique is a photothermal technique and subsurface defects are revealed by their interaction with the generated thermal wave. In these reported works, essentially single frequency modulation is used and surface displacement is measured at the output of a detection interferometer by monitoring a term at the second harmonic of the modulation frequency. The invention described in the present application applies instead to the detection of ultrasound and is not limited to essentially single frequency modulation. Measurement of surface deformation by monitoring a second harmonic term as described in these previous works restricts the usable modulation bandwidth to range from a given frequency to its second harmonic and is consequently of limited use. The invention described here does not rely on this approach.

Other important background information relevant to this invention relates to the method used for extracting the ultrasonic information of interest from the beam originating from the detection laser and reflected or scattered by the surface of the workpiece. Ultrasonic excitation of the object produces at its surface, small displacements which cause a phase or frequency perturbation on the scattered or reflected beam. Since the displacements are quite small, the optical phase or frequency discriminator has to be very sensitive; thus, in practice should be based on optical interferometry. Furthermore, the probed surfaces are rough, so the ultrasonic information is encoded into an optical beam with speckle and a suitable interferometric technique should integrate effectively over the whole speckle field or provide demodulation independently of speckle nature of the collected light beam. In various US patents the applicant (J.-P. Monchalin) has described interferometric schemes for sensitive detection in these conditions. In an arrangement described by the applicant in U.S. Pat. No. 4,659,224 issued Apr. 21, 1987, entitled "Optical Interferometric Reception of Ultrasonic Energy", a confocal Fabry-Perot is used in transmission to provide a signal representative of the surface motion independently of the speckle effect. In U.S. Pat. No. 4,966,459 issued Oct. 30, 1990, entitled "Broadband Optical Detection of Transient Surface Motion From a Scattering Surface", J.-P. Monchalin describes the use of the same type of interferometer, that may be used within a Mach-Zehnder interferometric arrangement or in a reflection scheme to provide the same capability with a very broad detection bandwidth. Still, a broader detection bandwidth, especially including the low ultrasonic frequency range, several kHz to about 1 MHz, is described by J. P. Monchalin and R. K. Ing in U.S. Pat. No. 5,131,748 issued Jul. 21, 1992, entitled "Broadband Optical Detection of Transient Motion from a Scattering Surface"and based on the use of two-wave mixing in a photorefractive crystal. Still another approach using a photorefractive crystal is described by I. A. Sokolov, S. I. Stepanov and G. S. Trofimov, in the Journal Opt. Soc. Am. B, Vol. 9, No. 1, January 1992, p.p. 173–176. In this approach the crystal performs the optical phase demodulation without the use of an optical detector and a voltage (photo-electromotive force) representative of the phase modulation of the detected signal beam appears on two electrodes at the surface of the crystal.

It is an object of the invention to provide a preferred laser ultrasonic apparatus and method for inspecting and characterizing materials.

SUMMARY OF THE INVENTION

In accordance with the invention, a method is provided for generating and detecting ultrasound on a workpiece, comprising the steps of:

a) providing a first pulsed laser beam;

b) providing a second pulsed laser beam;

c) modulating the first pulsed laser beam with a modulation signal;

d) directing the first modulated pulsed beam at a workpiece to generate ultrasound, the pulse duration of the pulsed beam being longer than an ultrasonic propagation time that is defined to be:

(i) the time of propagation of ultrasound from a generation location to a flaw or discontinuity to be detected within the workpiece and then to a detection location, or, (ii) the time of propagation of ultrasound directly from the generation location to the detection location;

e) directing the second pulsed laser beam, having a pulse duration longer than the ultrasonic propagation time, at the workpiece;

f) receiving phase modulated light from second pulsed laser beam reflected or scattered by the workpiece;

g) demodulating the received phase modulated light to obtain a demodulation signal representative of the ultrasonic motion at the surface of the workpiece; and, h) electronically processing said demodulation signal.

In accordance with another aspect of the invention there is provided an apparatus for generating and detecting ultrasound on a workpiece, comprising:

means for generating first and second pulsed laser beams, the pulse duration of the first laser beam being longer than an ultrasonic propagation time that is defined to be:

(i) the time of propagation of ultrasound from a generation location to a flaw or discontinuity to be detected within the workpiece and then to a detection location, or, (ii) the time of propagation of ultrasound directly from the generation location to the detection location, the pulse duration of the second beam being longer than the ultrasonic propagation time; means for modulating the first pulsed laser beam with a modulation signal; means for receiving phase modulated light from second pulsed laser beam reflected or scattered by the workpiece and for demodulating the received phase modulated light to obtain a demodulation signal representative of the ultrasonic motion at the surface of the workpiece; and, means for electronically processing said demodulation signal.

BRIEF DESCRIPTION OF THE DRAWINGS

Exemplary embodiments of the invention will now be described in conjunction with the drawings, in which.

DETAILED DESCRIPTION

Figure 1:
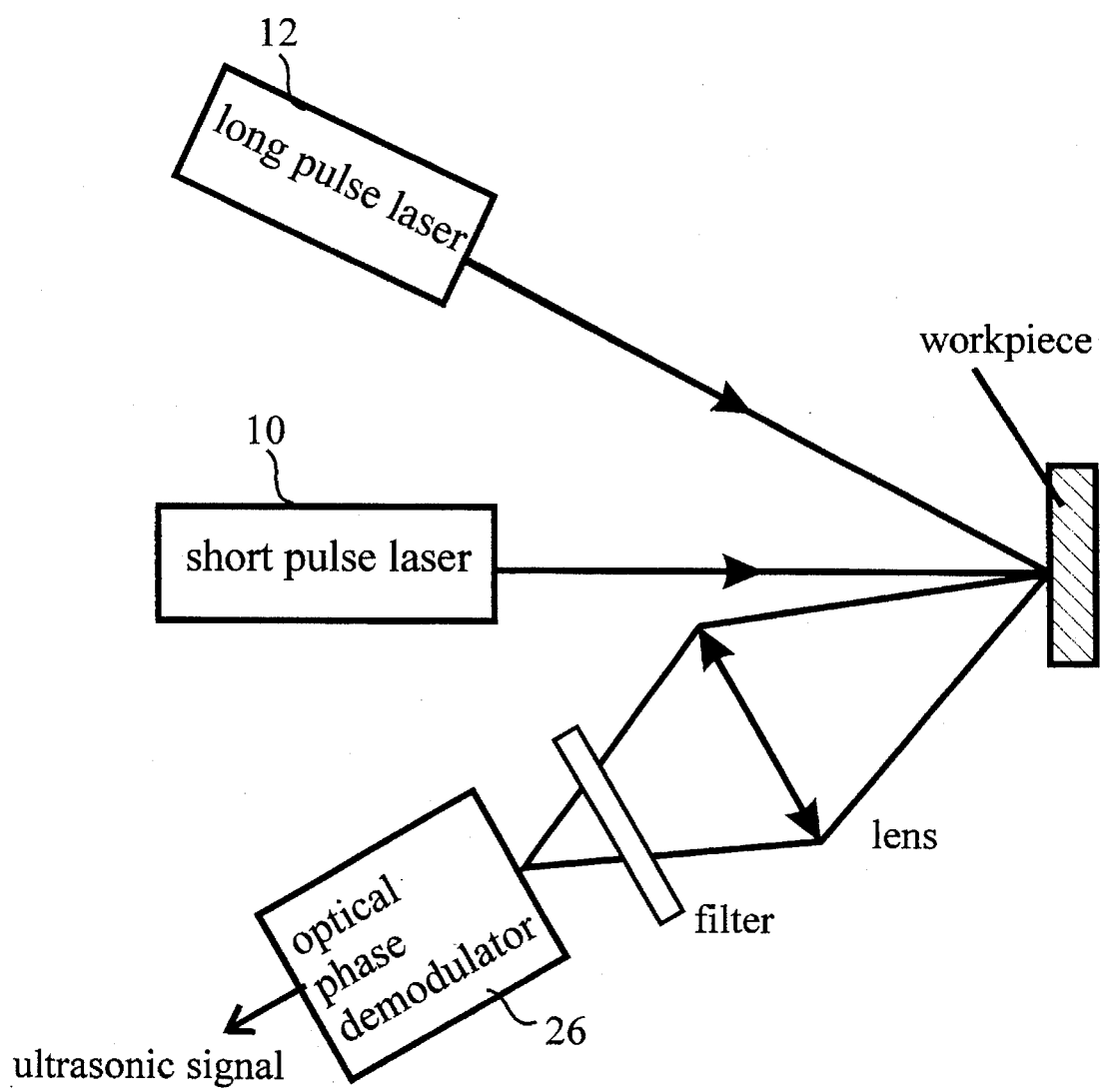
FIG. 1 is a prior art schematic block diagram illustrating an ultrasonic generation and detection apparatus including a long pulse detection laser and a short pulse generation laser.
Figure 2:
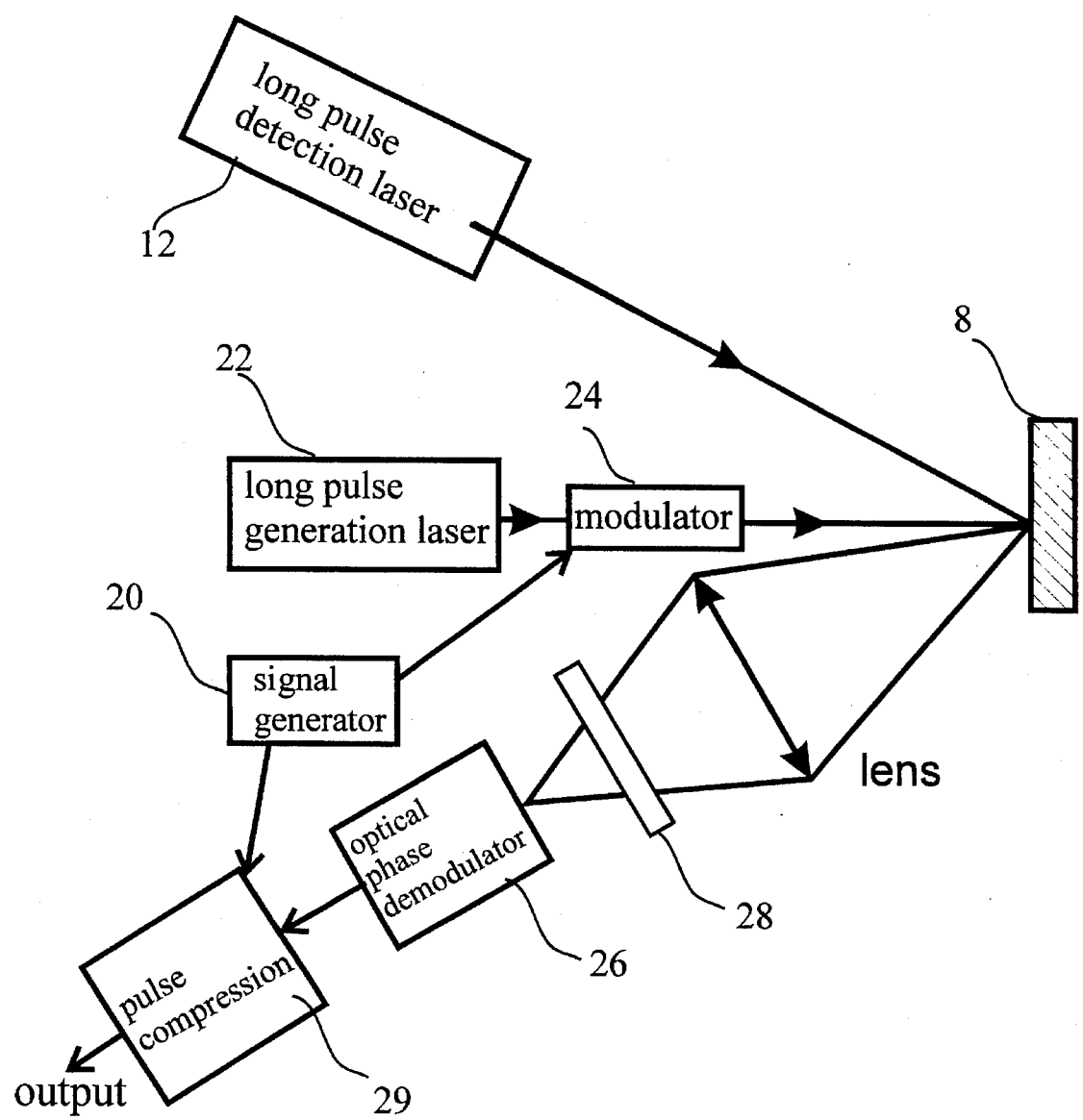
FIG. 2 is a schematic block diagram illustrating a first embodiment of an ultrasonic generation and detection apparatus including a long pulse detection laser, and a long pulse generation laser coupled to a modulator in accordance with the invention.

Referring first to FIG. 2, a long pulse generation laser 22 having a pulse length typically of 10 μs and higher is modulated in intensity by a modulator 24 (electro-optic or acousto-optic) driven by a signal generator 20 coupled to it. Although in some cases the modulation signal could be of single frequency, signals having a broader spectrum are generally used and needed to resolve the various ultrasonic echoes or ultrasonic modes given by the workpiece as described below. A useful modulation signal is the one corresponding to a frequency chirp, for example, a signal having an instantaneous frequency varying linearly with time. Other modulation codes could be used as well. The modulated beam is directed towards the surface of a workpiece 8, where it is partially absorbed at the surface or in its vicinity. The modulated beam provides an ultrasonic source by thermal expansion; the ultrasonic source has a time variation that follows the modulation signal, but is not identical to it, since the generation mechanism is usually frequency dependent.

Ultrasound then propagates at the surface and inside the workpiece 8 and is reflected by discontinuities such as flaws, edges or the back wall of the workpiece. It is then detected at the same location as generation or at another location by the detection laser. A detection laser 12 also having a long pulse (typically 10 μs or more) operates at a wavelength different from the generation laser. Scattered or reflected light from this laser 12 is finally collected and provided to an optical phase demodulator 26 that can be of any type mentioned heretofore, in the background section. A light filter 28 (interference, colored glass or other type) is used to block the light at the wavelength of the generation laser 22, while letting light at the detection wavelength pass through, so any adverse effect occurring at detection caused by the reception of modulated light from the generation laser is avoided.

Since the generation pulse is long (longer than the propagation time defined above), multiple reflections from the back wall or edges, or flaws or the various plate modes, may become mixed, thus the signal provided at the output of the optical phase demodulator may show a very complex time variation. It may then be difficult to identify echoes or to extract useful information from this raw signal and signal processing may be needed. The type of processing needed and used is similar to that used for Radar (for example described in a text entitled *Introduction to Radar Systems* by Merill I. Skolnik, 2nd edition, McGraw-Hill Book Company, 1980) and is called pulse compression. Pulse compression circuitry in the form of a filter 29 is shown coupled to the optical phase demodulator 26 in FIG. 2. The filter 29 is used to compress the output signal in time, so the various echoes or modes can be resolved. If generation, propagation in the workpiece or at its surface and detection are frequency independent, the transfer function of the filter to be used is actually the complex conjugate of the modulation signal spectra, i.e. it can be readily implemented by performing a cross-correlation of the output signal with the modulation signal which drives the intensity modulator. This simple operation yields reasonable results when the frequency bandwidth of the modulation signal is limited. Although cross-correlation can be done by analog means, current technology allows it to be performed efficiently and rapidly numerically.

In the case where higher modulation bandwidth is used, which could improve time resolution, the frequency dependence at generation, propagation and detection should be taken into account and the filter that is used should be modified. This can be performed numerically by using theoretical or known information relating to the frequency dependence associated with generation, propagation and detection. For example, in the case of a material absorbing strongly underneath a transparent layer of thickness d, which is the case of generation by a visible or near-infrared laser on graphite-epoxy where the strongly absorbing carbon fibers are found below a transparent epoxy layer, the frequency dependence of generation is represented by the function $\sin(2\pi fd/v)/f$, where f is the ultrasonic frequency and v is the acoustic velocity. The dependence of generation is also known for the generation of surface or plate waves on metal when the generation spot is a small line of a given width. As examples of known frequency dependencies for propagation, those of graphite-epoxy and metals could be mentioned. In graphite-epoxy, the attenuation coefficient in the usual MHz range is proportional to frequency, whereas for metals, attenuation depends upon grain size and has a variation that ranges typically from $f^2$ to $f^4$. Finally, for demodulation (i.e. detection), the theoretical frequency dependence is also well known for practical demodulators. Therefore, in many cases of interest, the frequency dependence is known and can be readily used to correct the filtering function. It is also possible, having modified the compression filter using theoretical or previously known information, to improve it further by using an empirical approach, consisting of making modifications to the filtering function and then in observing the performance of the new filter on actual experimental data. Further, in case where the generation laser can be operated with a very short pulse, the observed output signal provides the impulse response of the whole system including generation, propagation and detection, from which the correction to the compression filter can be readily derived.

Figure 3:
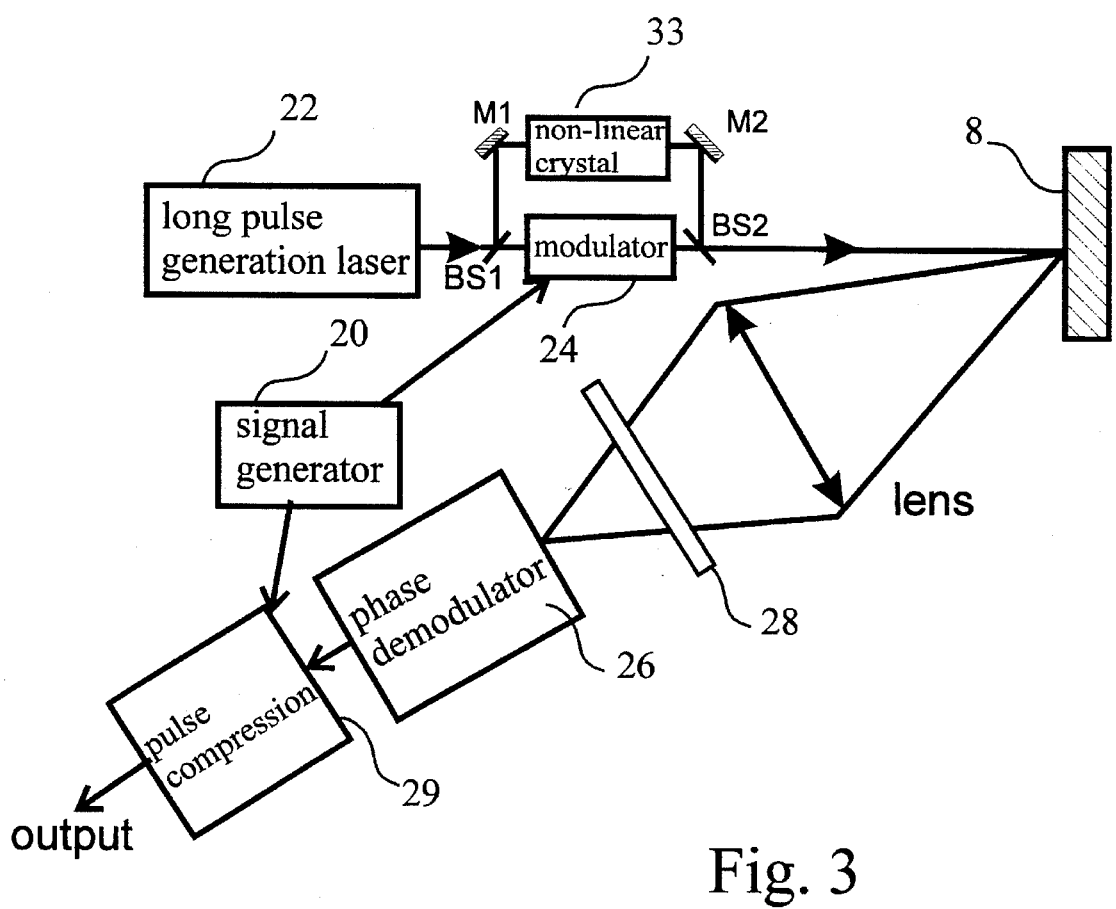
FIG. 3 is a schematic block diagram illustrating a second embodiment of an ultrasonic generation and detection apparatus having a single long pulse generation/detection means in accordance with the invention.

Turning now to FIG. 3 a second embodiment of the invention is shown wherein a single laser 22 is required. The laser beam is separated into two secondary beams by a first beam splitter BS1. A first beam is modulated as is described above and is used to generate ultrasound. The second beam is reflected off a mirror M1 into a nonlinear crystal 33. A mirror M2 then directs the beam to a second beam splitter BS2. The optical frequency of the second beam is changed by using a frequency shifting technique based on nonlinear optics, for example, and as is shown using the nonlinear crystal 33. This frequency shifting technique may be second harmonic generation known as an efficient and well developed technique. The two secondary beams are then recombined collinearly by the beam splitter BS2 to provide generation and detection at the same location. The other elements of this embodiment are the same as the ones found in FIG. 2 and have been described above.

Figure 4:
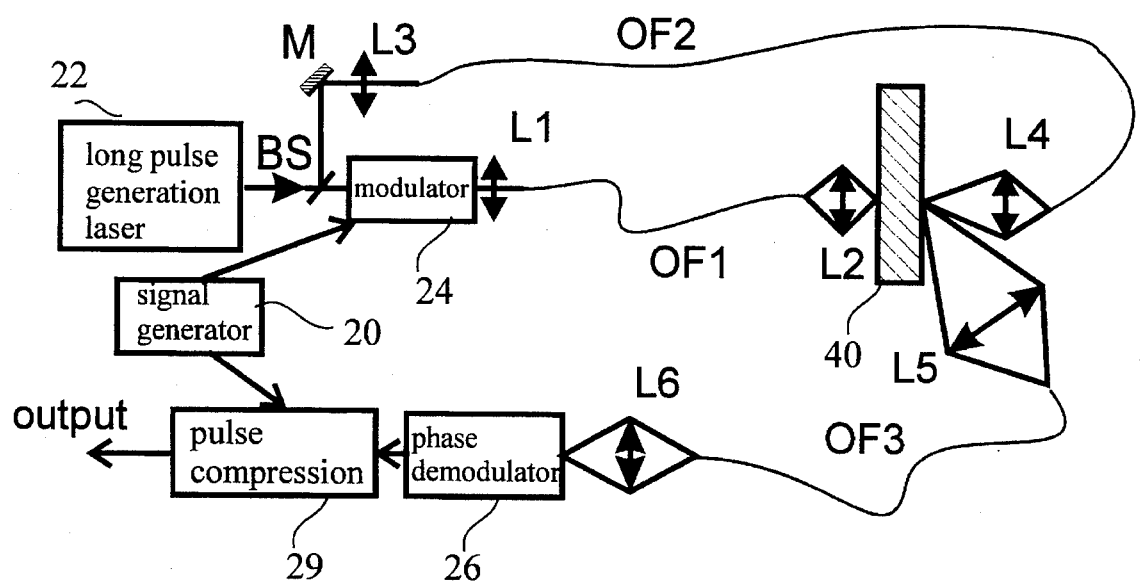
FIG. 4 is a schematic block diagram illustrating a third embodiment of an ultrasonic generation and detection apparatus utilizing optical fibers as light transmission paths, and wherein a generation laser beam and a detection laser beam from a single laser are directed at opposite sides of a workpiece.

Turning now to FIG. 4 a third embodiment of the invention is shown also using one laser 22 for generation and detection. Here however, generation and detection are performed on opposite sides of the workpiece 40, which is assumed, as is usually the case, to be opaque to laser light. The ultrasonic propagation time mentioned above corresponds in this case to the propagation time across the thickness of the workpiece. This embodiment shows also the use of optical fibers OF1, OF2, and OF3 for generation and detection. Optical fibers can also be used in the previous embodiments, but are preferred in this embodiment for convenient laser illumination on opposite sides of the workpiece. In operation, the configuration in FIG. 4 functions as follows: the laser beam is first split into two secondary beams by a beam splitter BS. A first beam is modulated by a modulator 24 and focused into an optical fiber OF1 by a lens L1. Modulated light transmitted by the fiber OF1 is then projected onto the surface of the workpiece by another lens L2, where it generates ultrasound. A second beam is coupled by a lens L3 into another optical fiber OF2. The light transmitted by this fiber is projected by a lens L4 onto the opposite surface of the workpiece for detection of ultrasound. Scattered light is collected by a larger lens L5 and transmitted by a third optical fiber OF3 and lens L6 onto an optical phase demodulator 26. A detected signal is processed as described above. This arrangement is very flexible and allows the laser and electronic hardware to be located at a distance as great as several tens of meters from the workpiece.

It should be noted that such a system can be readily mounted on existing mechanically scanned ultrasonic inspection stations for composite components used in the aeronautic industry. These inspection stations use conventional piezoelectric transducers and water jets for ultrasonic coupling. There is one transducer on each side of the inspected part and an ultrasonic transmission image of the part is obtained by mechanically scanning the transducers. The conventional transducers can be advantageously replaced by the lenses and the coupling fibers shown in FIG. 4 for performing without any water coupling ultrasonic inspection in transmission. This novel arrangement will be particularly useful to inspect contoured parts, since the conventional technique requires near-normal orientation of the water jets with respect to the surface of the part, which is not required with the laser ultrasonic approach described here.

Figure 5:
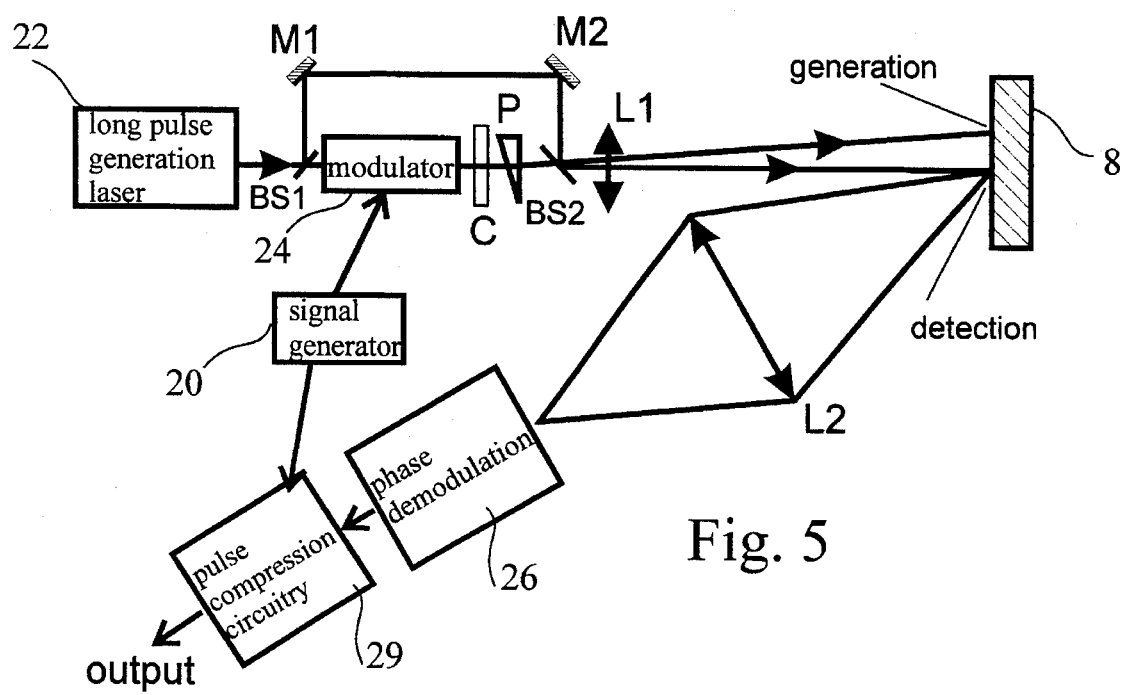
FIG. 5 is a schematic block diagram illustrating a fourth embodiment of an ultrasonic generation and detection apparatus in accordance with this invention, wherein generation and detection are performed at different locations on the same side of a workpiece.

Yet another embodiment of the invention is shown in FIG. 5, using in this case surface or plate waves to probe the workpiece 8. Here, generation and detection are performed on the same surface of the workpiece 8 but at different locations. As shown in FIG. 5, the arrangement is similar to the one shown in FIG. 3, however does not require frequency shifting by a non-linear crystal. The modulated secondary beam is used for ultrasound generation. Both secondary beams pass through a lens L1 and are focused onto a sufficiently small spot (smaller than the acoustic wavelength of the generated surface or plate wave) at the surface of the workpiece 8. Generation and detection are performed at different locations separated by a well defined distance by adding a beam deflection device before the lens L1 and the mixing beam splitter BS2 in the modulated or unmodulated secondary beam path. FIG. 5 shows the use of a prism P for beam deflection in the modulated secondary beam path between the modulator 24 and the mixing beam splitter BS2. FIG. 5 shows a configuration where the generation spot is essentially circular. It is often advantageous to generate the acoustic wave in a preferential direction. This is readily obtained by adding a cylindrical lens C before or after the deflecting prism P, in such a way that a small line (in a direction perpendicular to the plane of the drawing) is obtained at the surface of the workpiece 8. Detection and processing is performed as described above. In this case since generation and detection are performed at the same wavelength, it is important that the collection optics be provided with adequate field stops, so the optical phase demodulator 26 does not receive any intensity modulated light from the generation beam. A phase demodulator which is not sensitive to intensity modulation is also advantageous in this case.

The arrangement shown in FIG. 5 is particularly useful for measuring material anisotropy, such as the anisotropy or texture of a steel (or other metal) sheet, which is an important parameter for deep drawing. It is known that such anisotropy can be evaluated from the measurement of the acoustic velocities of waves propagating along various directions at the surface of the specimen. In the embodiment of FIG. 5 a pulsed beam is provided by the distance between generation and detection being well defined, the velocity in the direction determined by the generation and detection spots is deduced from the measurement of the time of propagation between generation and detection. To obtain the velocity in a different direction the deflecting prism P and the associated cylindrical lens C are rotated around the beam axis before deflection. This embodiment has the advantage compared to the usual scheme, which uses two lasers, one with a short pulse for generation and another one with a long pulse for detection, to provide a well defined and very stable distance between generation and detection, allowing accurate determination of velocity and anisotropy effects. When using two lasers, limitations in the pointing stability of the lasers makes this separation distance to vary slightly in time, resulting in limited accuracy for velocity determination.

It should be noted that there are cases for which the embodiment of FIG. 5 is used where simple sine modulation (single frequency) could be used. This occurs when the edges of the workpiece are sufficiently remote and a single propagation mode is excited. In this case, although pulses in the 50 μs range are used no echo overlapping occurs. Propagation delay between generation and detection can be accurately determined by cross-correlating the signal at the output of the optical phase demodulator with the modulation signal. Propagation delay is determined modulo-one modulation period. This uncertainty can be removed by measuring the delay associated with the pulse envelope, which can be determined by cross-correlating the envelope of the received signal with the laser pulse.

Figure 6:
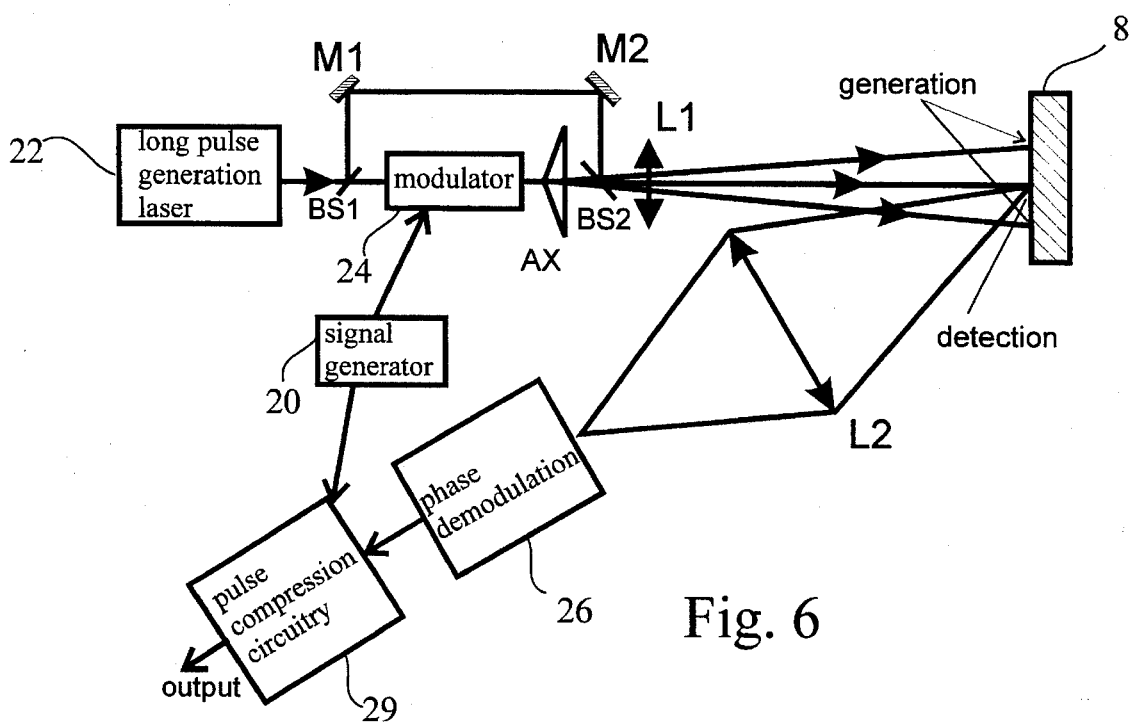
FIG. 6 is a is a schematic block diagram illustrating a fifth embodiment of an ultrasonic generation and detection apparatus in accordance with this invention wherein generation is performed on a circle at the surface of a workpiece and detection is performed at the center of the circle; and, FIG. 7 is a is a schematic block diagram illustrating a sixth embodiment of an ultrasonic generation and detection apparatus in accordance with this invention including acousto-optical frequency shifting means and photorefractive crystal detection.

Yet, another embodiment of the same invention, which provides an important increase of sensitivity, is shown in FIG. 6. In this embodiment, as shown in FIG. 6 and as explained in U.S. Pat. No. 4,541,280 entitled "Efficient laser generation of surface acoustic waves" by P. G. Cielo and J. F. Bussière, a ring source is produced at the surface of the workpiece by an axicon AX (conical lens) and strong normal displacement is produced at its center where detection is performed. For the purpose of measuring anisotropy, the use of a full ring source is obviously not adequate, but the axicon could be masked for this purpose to produce two small circular arcs. The mask could be rotated to measure velocity in various directions, thus providing an evaluation of material anisotropy.

Figure 7:
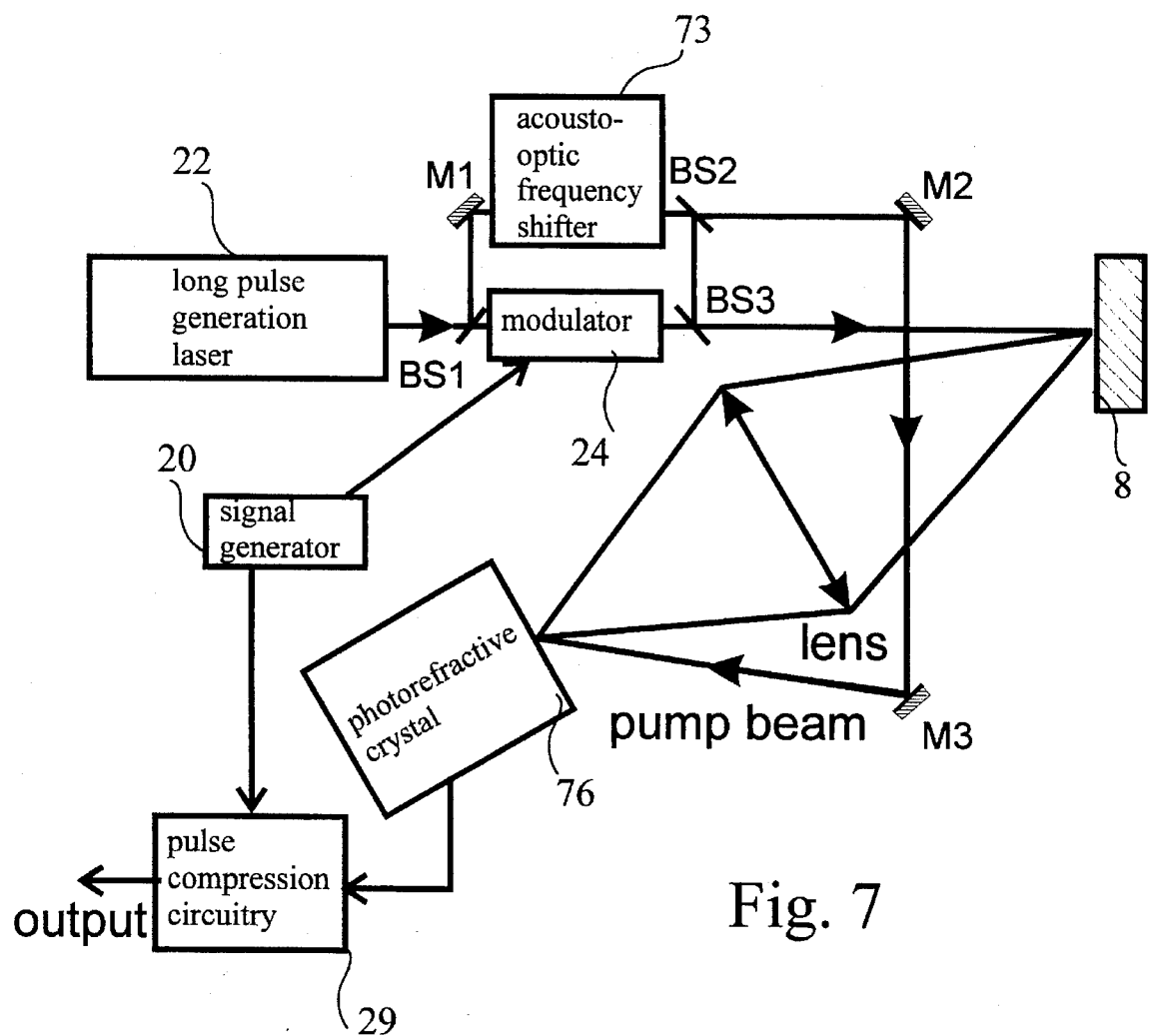

A last embodiment of the same invention is shown in FIG. 7. This embodiment is similar to that of FIG. 3 with the exception of two primary features. The nonlinear crystal 33 of FIG. 3 is replaced in FIG. 7 by acousto-optic frequency shifter 73, that only slightly changes the laser frequency (for example by an RF value approximately within the range of 40–300 MHz). This frequency shifted beam is used for detection. Since the change in frequency is small, the modulated frequency unshifted beam scattered by the surface cannot be blocked in front of the optical phase demodulator by a filter. Therefore the optical phase demodulator 76 receives, besides the phase modulated beam to be detected, a spurious and strong intensity modulated beam. Although differential schemes, as explained in U.S. Pat. No. 5,131,748 mentioned above and U.S. Pat. No. 5,080,491 entitled "Laser optical ultrasound detection using two interferometer systems" by J. P. Monchalin and R. Héon, are known, they are not sufficiently efficient to eliminate the strong amplitude modulation signal present in this case. However applicants have found that an optical demodulator based on the use of the induced photoelectromotive force in a photorefractive crystal (mentioned above) permits detection of the ultrasonic signal without any adverse effect of the strong intensity modulated beam received by the phase demodulator 76 in the form of a crystal. As shown in FIG. 7, a fraction of the frequency shifted beam, obtained through beam splitter BS2, is used as pump beam for the photorefractive crystal 76. This pump beam interferes inside the crystal with the beam at the same frequency reflected or scattered by the surface to produce an electric charge grating. The photoelectromotive force signal representative of the ultrasonic surface motion appears on electrodes attached to the crystal 76. It should be noted that although suitable crystals for this purpose are usually photorefractive (i.e. give rise to an index of refraction grating), the basic requirement is the creation of an electric charge grating. A crystal which does not give rise to an index of refraction grating by its symmetry properties may also qualify. The output signal is processed as before. It should be also noted that the important fact for successful operation of the demodulator/crystal 76 in this case, is to avoid the creation of a photorefractive grating by the reflected or scattered generation beam. This is obtained by providing a sufficiently large frequency shift to the detection and pump beam. The condition to satisfy is to provide a shift higher than the low frequency cut-off of the photorefractive crystal. In some cases, particularly when the crystal has a slow response (low frequency cut-off below 1 kHz), this shift can also be provided by using the Doppler effect and reflecting the detection and pump beams off a mirror mounted on a piezoelectric pusher excited by a ramp voltage. If there is no depolarization effect by the surface, the same result could also be obtained by polarizing the generation and detection beams along perpendicular directions, so the reflected or scattered generation beam does not interfere with the pump beam inside the crystal 76.

Of course, numerous other embodiments may be envisaged, without departing from the spirit and scope of the invention.

What we claim is:

1. A method for generating and detecting ultrasound on a workpiece, comprising the steps of:

a) providing a first pulsed laser beam;

b) providing a second pulsed laser beam;

c) modulating the first pulsed laser beam with a modulation signal;

d) directing the first modulated pulsed beam at a workpiece to generate ultrasound the pulse duration of the pulsed beam being longer than an ultrasonic propagation time that is defined to be:

(i) the time of propagation of ultrasound from a generation location to a flaw or discontinuity to be detected within the workpiece and then to a detection location, or, (ii) the time of propagation of ultrasound directly from the generation location to the detection location;

e) directing the second pulsed laser beam, having a pulse duration longer than the ultrasonic propagation time, at the workpiece;

f) receiving phase modulated light from the second pulsed laser beam either reflected or scattered by the workpiece;

g) demodulating the received phase modulated light to obtain a demodulation signal representative of the ultrasonic motion at the surface of the workpiece; and, h) electronically processing said demodulation signal.

2. A method as defined in claim 1 wherein a pulse compression filter is utilized in the processing step (h) to separate ultrasonic echoes.

3. A method as defined in claim 1, wherein the processing step includes separating ultrasonic echoes by cross correlating the demodulation signal with said modulation signal.

4. A method as defined in claim 2, where the pulse compression filter is modified to compensate for at least frequency dependence of ultrasonic generation at the surface of the workpiece, frequency dependence of ultrasonic propagation inside or at the surface of the workpiece or frequency dependence of demodulation by optical means.

5. A method for generating and detecting ultrasound on a workpiece, as defined in claim 1, wherein the first modulated pulsed laser beam and the second pulsed laser beam are derived from a single unmodulated pulsed beam by separating the unmodulated pulsed beam into the first and second pulsed beams, prior to said modulating step (c).

6. A method as defined in claim 5, including the step of changing the wavelength of one of the first and second pulsed laser beams such that the wavelengths of the first and second beams are of different wavelengths.

7. A method as defined in claim 5, wherein the first and second pulsed laser beams are directed towards opposite sides of the workpiece.

8. A method as defined in claim 5, wherein the first and second pulsed laser beams are directed onto different locations on a same surface of the workpiece.

9. A method as defined in claim 8, wherein the first pulsed modulated laser beam is projected on a circle or part of a circle at the surface of the workpiece and the second pulsed laser beam is directed at the center of the circle for detection of the converging ultrasonic wave.

10. A method as defined in claim 5, comprising the steps of:

changing the frequency of the second laser beam by an electronically excited frequency shifting means;

removing a pump beam from the second pulsed laser beam; and, wherein the demodulation step includes allowing the phase modulated light reflected or scattered by the workpiece and the pump beam to interfere inside a crystal to produce an electric charge grating, the demodulation signal representative of the ultrasonic motion at the surface of the workpiece being obtained from an induced photoelectromotive force detected across the crystal.

11. An apparatus for generating and detecting ultrasound on a workpiece, comprising:

means for generating first and second pulsed laser beams, the pulse duration of the first laser beam being longer than an ultrasonic propagation time that is defined to be:
(i) the time of propagation of ultrasound from a generation location to a flaw or discontinuity to be detected within the workpiece and then to a detection location, or,
(ii) the time of propagation of ultrasound directly from the generation location to the detection location, the pulse duration of the second beam being longer than the ultrasonic propagation;

means for modulating the first pulsed laser beam with a modulation signal;

means for receiving phase modulated light from second pulsed laser beam reflected or scattered by the workpiece and for demodulating the received phase modulated light to obtain a demodulation signal representative of the ultrasonic motion at the surface of the workpiece; and, means for electronically processing said demodulation signal.

12. An apparatus as defined in claim 11, wherein the processing means comprises a pulse compression filter for separating ultrasonic echoes.

13. An apparatus as defined in claim 11, wherein the processing means performs a cross correlation of the demodulation signal with said modulation signal.

14. An apparatus as defined in claim 12, where the processing means includes means to modify the pulse compression filter for compensation of at least frequency dependence of ultrasonic generation at the surface of the workpiece, frequency dependence of ultrasonic propagation inside or at the surface of the workpiece or frequency dependence of demodulation by optical means.

15. An apparatus for generating and detecting ultrasound on a workpiece, as defined in claim 11, wherein the means for generating the first and second pulsed laser beams, include means for generating an unmodulated pulsed laser beam, and means for splitting the unmodulated laser beam into the first and second pulsed laser beams.

16. An apparatus as defined in claim 15, further comprising an element having non-linear properties for changing the wavelength of the second pulsed laser beam directed through it.

17. An apparatus as defined in claim 16 further comprising filter means disposed between the workpiece and the means for receiving and demodulating the phase modulated light, said filter means for substantially preventing the first pulsed modulated laser beam light from being received by said means for demodulating.

18. An apparatus as defined in claim 15, including light guiding means for directing the first and second pulsed laser beams towards opposite sides of the workpiece.

19. An apparatus as defined in claim 15, further including direction shifting means and focusing means to direct first modulated laser beam and second pulsed laser beams onto different locations on the same surface of the workpiece.

20. An apparatus as defined in claim 15, further including means to project the first modulated beam onto a circle or part of a circle at the workpiece, and, focusing means to project second laser beam at the center of the circle for detection of the converging ultrasonic wave.

21. An apparatus as defined in claim 15, including:

means to shift the frequency of one of the first and second laser beams such that the first and second laser beams are of different frequencies;

means to remove a pump beam from second pulsed laser beam;

the demodulation means being in the form of a crystal for receiving phase modulated light reflected or scattered by the workpiece and the pump beam, and for demodulating the phase modulated light, the crystal having electrodes for providing a photoelectromotive force signal across them generated within the crystal that is representative of the ultrasonic motion at the surface of the workpiece.

22. An apparatus as defined in claim 21 wherein means to shift the frequency of one of the first and second laser beams is an acousto-optic cell.

23. An apparatus as defined in claim 21 wherein the crystal is a photorefractive crystal.

* * * * *